United States Patent
Middlesworth et al.

(10) Patent No.: US 8,057,879 B2
(45) Date of Patent: Nov. 15, 2011

(54) STRETCHABLE WEB

(75) Inventors: Jeffrey Alan Middlesworth, Wauconda, IL (US); Stephen Donald Bruce, Montpelier, VA (US); Tze Wan Pansy Chung, Fox River Grove, IL (US); James D. Tribble, Brazil, IN (US)

(73) Assignee: Tredegar Film Products Corporation, Richmond, VA (US)

( * ) Notice: Subject to any disclaimer, the term of this patent is extended or adjusted under 35 U.S.C. 154(b) by 740 days.

(21) Appl. No.: 11/982,144

(22) Filed: Nov. 1, 2007

(65) Prior Publication Data

US 2008/0063837 A1 Mar. 13, 2008

Related U.S. Application Data

(62) Division of application No. 10/807,409, filed on Mar. 24, 2004, now abandoned.

(60) Provisional application No. 60/457,825, filed on Mar. 26, 2003.

(51) Int. Cl.
*B32B 3/24* (2006.01)

(52) U.S. Cl. ......... 428/137; 428/134; 428/135; 428/136

(58) Field of Classification Search .................. 428/134, 428/135, 136, 137
See application file for complete search history.

(56) References Cited

U.S. PATENT DOCUMENTS

| | | | |
|---|---|---|---|
| 5,518,801 A | | 5/1996 | Chappell et al. |
| 5,702,798 A | * | 12/1997 | Sugita et al. ................. 428/131 |
| 5,804,021 A | | 9/1998 | Abuto et al. |
| 5,997,986 A | | 12/1999 | Turi et al. |
| 6,452,063 B1 | | 9/2002 | Curro et al. |
| 6,468,630 B1 | | 10/2002 | Mishima et al. |
| 6,472,045 B1 | | 10/2002 | Morman et al. |
| 2001/0005540 A1 | | 6/2001 | Hisanaka et al. |
| 2001/0008676 A1 | | 7/2001 | Pelkie et al. |
| 2003/0003269 A1 | | 1/2003 | Lee et al. |
| 2003/0021951 A1 | | 1/2003 | Desai et al. |
| 2004/0005835 A1 | | 1/2004 | Zhou et al. |
| 2005/0003152 A1 | | 1/2005 | Thomas et al. |

FOREIGN PATENT DOCUMENTS

| | | |
|---|---|---|
| WO | 99/62449 A2 | 12/1999 |
| WO | 2004/087409 A1 | 10/2004 |

* cited by examiner

*Primary Examiner* — William P Watkins, III

(57) ABSTRACT

The present invention relates to stretchable webs having a plurality of elongated cells, and a retractive force mechanism to provide increased retractive force of the web when stretched in a given direction. The stretchable webs are useful in disposable garments such as diapers, bandages and other hygiene material so that the material fits closely without slipping off.

6 Claims, 14 Drawing Sheets

STRETCHABLE WEB

BACKGROUND OF THE INVENTION

1. Technical Field of the Invention

This invention relates generally to stretchable webs and more particularly to a stretchable web for use in garments that are manufactured with materials of relatively low elasticity. The invention also relates to laminates including the stretchable webs, where the laminates have relatively low elasticity.

2. Description of Related Art

Stretchable Webs are useful in disposable and non-disposable garments for increasing comfort and fit of the garments. Such stretchable webs are used in armbands, waistbands and other panels of a garment. Stretchable webs may also be used throughout a garment to make the overall garment have a more comfortable drape.

Stretchable webs that typically are employed in disposable and non-disposable garments include elastic materials. A major drawback of elastic materials is the cost of manufacturing such materials. Therefore, it is desirable to have a stretchable web that is manufactured of lower cost materials that can perform as required for various applications. Another disadvantage of elastic materials is that elastic materials typically stretch in all directions, thus requiring extra care during processing.

Netting materials are known in the art that provide some elasticity, but are known to have poor retractive qualities. In other words, netting materials are known to extend easily when a biasing force is placed in a particular direction, but the retractive force is not sufficient to meet many applications where elastic materials are used. Therefore, it would be advantageous to have a netting material created of inelastic materials that have sufficient forces to replace more expensive elastic materials.

U.S. Pat. No. 6,452,063, to Curro et al., the disclosure of which is incorporated herein by reference in its entirety, discloses a three-dimensional apertured elastic web having elongated apertures. The web is stretchable in a direction perpendicular to the major axis of the elongated apertures. While affording good stretching characteristics, this three-dimensional web has poor recovery.

Other drawbacks of the three-dimensional web of the '063 patent include reduced stretchability properties due in part to the aspect ratio of the apertures (length of the major axis to the minor axis) being within the range of from about 1.5 to about 5. Moreover, because these 3-dimensional webs have polygonal shaped cells that can stretch in various directions, they require extra care during processing. Additionally, this three-dimensional web does not provide sufficient recovery after stretching in a given direction. Thus, the three-dimensional web would be of little use in closely fitting disposable garments such as diapers that require good stretchability as well as good recovery so that the garment fits closely without slipping.

The description herein of certain disadvantages associated with known materials, webs, methods, and apparatus is not intended to limit the invention to embodiments that do not include the known items. Indeed, various aspects of the invention may include one or more of the known materials, webs, methods, and apparatus without suffering from the disadvantages described herein.

SUMMARY OF THE INVENTION

It is a feature of an embodiment of the invention to provide a stretchable web and/or laminate having sufficient retractive force to be used in garments requiring such properties (e.g., diapers and other close-fitting garments). It is an additional feature of another embodiment to provide webs and/or laminates that can be made from relatively inexpensive materials. These and other features are achieved by certain embodiments of the invention.

In accordance with these features of embodiments of the invention, there is provided a stretchable web including elongated cells with a major axis and a minor axis. The stretchable web comprises the elongated cells aligned to provide mechanical elasticity perpendicular to the aligned elongated apertures. The stretchable web further comprises a retractive force mechanism to provide increased retractive force in the direction of mechanical elasticity. Various embodiments described in the detailed description section below provide the requisite retractive force means to increase the retractive force of the web when it is stretched in the given direction.

In accordance with additional embodiments of the invention, there are provided laminates comprising the stretchable webs, and absorbent garments comprising the stretchable webs. Embodiments of the invention also include methods of making the stretchable web, as well as methods of making the laminates including the stretchable webs.

DETAILED DESCRIPTION OF THE EXEMPLARY EMBODIMENTS OF THE INVENTION

Figure 1:
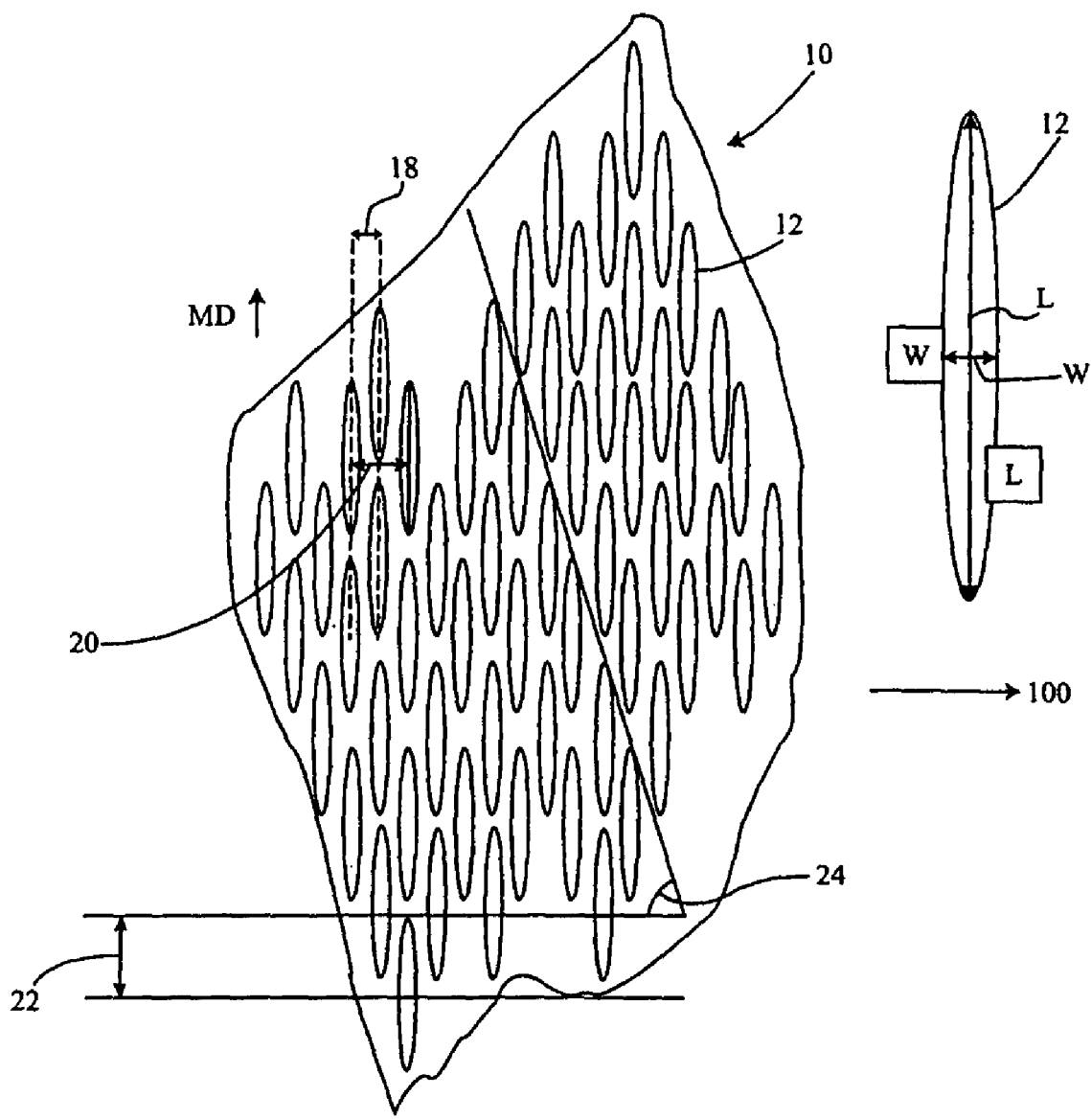
FIG. 1 is a plan view of a formed material used in creating the stretchable web of this invention.

As used herein, the term "elastic" refers to any material that upon application of a biasing force, is stretchable, i.e., elongatable. Preferably, the term "elastic" denotes a material that is stretchable at least about 60 percent (i.e., to a stretched, biased length that is at least about 160 percent of its relaxed unbiased length), and that will recover at least 55 percent of its elongation upon release of the stretching, elongation force. A hypothetical example would be a one (1) inch sample of a material that is elongatable to at least 1.60 inches, and upon being elongated to 1.60 inches and released, will recover to a length of not more than 1.27 inches. Many elastic materials may be elongated by more than 60 percent (i.e., much more than 160 percent of their relaxed length), for example, elongated 100 percent or more, and many of these materials will recover to substantially their initial relaxed length, for example, to within 105 percent of their initial relaxed length, upon release of the stretch force. All materials, whether elastic or not, will have a relative degree of elasticity as compared to other materials.

As used herein, the term "extensible" refers to any material that upon application of a biasing force, is stretchable in at least one direction, i.e., elongatable. Preferably, the term "extensible" describes a material that is stretchable to at least about 60 percent without suffering catastrophic failure (i.e., to a stretched, biased length that is at least about 160 percent of its relaxed unbiased length), but does not recover more than 55 percent of its elongation upon release of the stretching, elongation force.

As used herein, the term "garment" means any type of apparel that may be worn. The term garment includes industrial work wear and coveralls, undergarments, pants, shirts, jackets, gloves, socks, diapers, disposable undergarments, adult incontinence articles, feminine hygiene articles, and the like.

As used herein, the expression "non-woven web" refers to a web that has a structure of individual fibers or threads that are interlaid, but not in any regular, repeating manner. Non-woven webs in the past have been formed by a variety of processes such as, for example, melt-blowing processes, spun-bonding process, and thermo-bonded carded web processes.

As used herein, the expression "point bonding" denotes bonding one or more fabrics at a plurality of discrete points. For example, thermal point bonding generally involves passing one or more layers to be bonded together between heated rolls such as, for example an engraved pattern roll and an anvil (or smooth calendar) roll. The engraved roll is patterned on its surface in some way so that the entire fabric is not bonded over its entire surface, and the anvil roll usually has a flat or smooth surface. As a result, various patterns for engraved rolls have been developed for functional as well as aesthetic reasons. Point bonding would include, but is not limited to, other bonding methods such as small area adhesive addition, ultra sonic and pressure bonding.

As used herein, the expression "pressure bonding" refers to a process whereby a web (or webs) is placed between two elements that exert pressure on the web to bind the various components of the web (or webs) in the areas where pressure is being exerted.

As used herein, the term "substantially" means that a given property or parameter may vary by about 20% from the stated value.

As used herein, the expression "ultrasonic bonding" means a process performed, for example, by passing material between a sonic horn and an anvil roll as illustrated in U.S. Pat. No. 4,374,888 to Bomslaeger or in U.S. Pat. No. 5,591,278 to Goodman et al Ultrasonic bonding is well known in the art, and a variety of sonic horns and anvil are commercially available from, for example, Branson Ultrasonics, Danbury, Conn., etc. In general, these units produce high frequency vibration energy that melt thermoplastic components at the bond sites within the layers and join them together.

Throughout this description, the expression "retractive mechanism" denotes any mechanism, either a material, or a processing method, of increasing the retractive force of the web. Various retractive mechanisms are disclosed in this application, and the invention is intended to include the described mechanisms, as well as any other known or later discovered retractive mechanisms.

The invention relates generally to a stretchable web having elongated cells having a major axis and a minor axis. The web preferably is stretchable in a direction generally orthogonal to the major axis of the cells. The given stretchable direction may be in the machine direction (MD), cross direction (CD or TD), or at an angle between the machine direction and the cross direction. An additional embodiment below provides for improved handling characteristics of the stretchable web during the converting process.

A first embodiment of the web having a retractive mechanism incorporates lanes of unapertured film separating lanes of apertured film. This web is elongated in the cross direction and begins to contract in the machine direction, with the unapertured lanes resisting buckling and creating the desired cross direction retractive force. In a similar vein, sections of the web may have varying sized elongated cells.

A second embodiment of the stretchable web incorporates a non-woven or unapertured film layer attached at a plurality of discrete points. Again, the buckling force of this added layer creates the desired retractive force. The bonding at discrete points is preferably aligned in the machine direction to avoid inhibiting cross direction stretching. One version of this embodiment includes the addition of the non-woven in fluted or creped form during vacuum lamination, while another version uses extrusion lamination or coating with a non-woven, followed by IMG activation to weaken the laminate in the cross machine direction while retaining machine direction rigidity for buckling force. Another version of this embodiment utilizes slit or apertured non-woven materials. In the case of slitted non-wovens, it is preferred that the slits would be aligned with the elongated cells. Furthermore, incrementally stretched non-wovens may be used, such as intermeshing gear (IMG) activated non-wovens. As an additional consideration in this application, it can be beneficial to bond the non-wovens to the netting with elastomeric adhesives. Adhesives may be applied in a variety of patterns including zig-zag, linear, omega or spiral.

A third embodiment of the invention includes two layers of the stretchable web bonded together at discrete points or in segments to increase the buckling force and increase the cross-direction retractive force. This lamination can be accomplished by vacuum lamination of the two films with the elongated apertures or with any known bonding method. Additionally, the two layers of stretchable web may be offset such that the major axes of the elongated cells of the first layer is at an angle to the major axes of the elongated cells of the second layer. Finally, the two layers may have differing mesh counts and cell sizes.

A fourth embodiment of the stretchable web includes bridging elements extending across the elongated cells in the given direction. The bridging elements would resist expansion of the minor axes of the cells, thereby adding retractive force. The bridging elements can be formed in several ways. In a first implementation, the bridging elements may be formed of the same material as the stretchable web. The bridge may be three-dimensional or it may be two-dimensional in this implementation. In a second implementation, the bridging elements may be formed of strands of a separate material overlaying the stretchable web. These strands may be centered on the major axes of the elongated cells, or they may be applied without consideration of their location relative to the elongated cells. The strands may be of elastic materials such as LYCRA®, or elastic adhesives, or they may be comprised of an inelastic material.

Another consideration in forming bridging elements is the offset between adjacent bridging elements. The bridging elements may preferably have increased offsets of up to a little more than half the length of an elongated cell, or reduced offsets, that may be approximately one quarter the length of an elongated cell. One further consideration is that the bridging elements may be used to increase the stability of the web during handling and conversion processes. The bridging elements may be designed to maintain the integrity of the web during processing, but then be ruptured either by the user, or near the end of the processing, by stretching the web beyond the elastic limit of the bridging elements, but within the elastic limit of the web. This requires that the bridging elements have a lower threshold for stretching than the web. This can be achieved by selecting a more elastic material for the web and a less elastic material for the bridging element, or by making the bridging element relatively thin.

A fifth embodiment of the invention includes pinwheel grouping of cells. The pinwheel grouping preferably would include a center cell surrounded by at least two other cells. For example, two "C" shaped cells may partially surround a round cell in the center. Or, an elongated cell may be partially surrounded by four "comma" shaped cells. Additional cells may be used as well. This pinwheel design creates a cell within a cell so that the first cells may collapse and then the second, creating a staged reaction to the stretching and a staged retractive force as well. The stretchable web of the present invention comprises a web of inelastic material and pinwheel groupings of three-dimensional cells in the inelastic material including a central cell and a plurality of partially surrounding cells to create form elasticity.

As can be seen in FIGS. 2 through 11, a stretchable web 8 may be formed in part by a formed thermoplastic or elastomeric film or non-woven web 10. The formed film or non-woven web 10 preferably is combined with various retractive force mechanisms 26 to create a stretchable web 8 of the invention. A stretchable web of the present invention preferably comprises a three-dimensional web of inelastic material having elongated cells aligned to provide mechanical elasticity perpendicular to the aligned elongated apertures, and a retractive force mechanism to provide increased retractive force in the direction of mechanical elasticity. Although preferred embodiments of the invention include a three-dimensional web, skilled artisans will appreciate that the stretchable web may be a flat film formed to have elongated cells to impart stretchability thereto.

Referring now to FIG. 1, the formed film or non-woven web 10 includes a plurality of elongated cells 12. Elongated cells 12 typically are three dimensional with walls extending from a top surface of the web 10 towards a bottom surface. Elongated cells 12 are preferably apertured at the bottom surface. Elongated cells 12 have a major axis and a minor axis denoted by a length "L" and width "W," respectively. While the ratio between length "L" and width "W" may vary, in a preferred embodiment the length "L" is between about 5 and about 15 times the width "W", and in another embodiment length "L" is 10 times the width "W". As shown in FIG. 1, the cells 12 are aligned in an offset brick pattern with the major axes of the cells parallel to the machine direction. An advantage of having the major axes parallel to the machine direction is that the film is generally not stretchable in the machine direction and, therefore, is easier to handle when used in its intended commercial application. The major axes of elongated cells 12 may be aligned in any direction and the web 10 generally will have elasticity orthogonal to the direction of alignment of the major axis of cells 12.

Cells 12 can have a row spacing 18 between the offset rows. In a preferred embodiment, the row spacing 18 is approximately 1.75 mm, although such spacing may be varied greatly for various applications. Aligned cells 12 can have an aligned row spacing 20, and in a preferred embodiment is approximately 3.5 mm but can also vary greatly depending on the application. Aligned cells 12 may also have a length spacing 22, and in a preferred embodiment the length spacing is approximately 5.7 mm, but may vary with the application. The arrangement of elongated cells 12 can create an alignment angle 24 that is approximately 72° in a preferred embodiment, but again may vary greatly. The alignment angle preferably is the angle formed between: (i) a line intersecting the apex of apertures of adjacent cells in two rows; and (ii) a line parallel to the minor axis of the cells 12. Thus, if the cells 20 were not offset in consecutive rows, the alignment angle 24 would be zero.

The above described three-dimensional web 10 of FIG. 1 may also be described as a formed film netting material. An advantage of this netting material 10, is that it is a three-dimensional web such that the cells 12 have walls that extend in the z-direction (perpendicular to the plane of the netting material). As mentioned above, webs such as those described in the '063 patent typically will not have the requisite retractive force for many applications. Consequently, a retractive force mechanism 26 preferably is applied to the netting material 10 of various preferred embodiments of the invention to provide the requisite retractive force. Alternatively, the web 10 can be formed to have the requisite retractive force by one of offset rows of cells 20, lanes of unapertured material, varying sizes of cells 20 and the like.

Formed film 10 can be composed of variety of thermoplastic materials, and preferably a relatively inelastic thermoplastic material. In a preferred embodiment polyethylene has been used. Other polymers can be used, including, for example, copolymers of polyethylene with other monomers, like propylene, butylene, and the like, polyproplyene homopolymers or copolymers of polypropylene and butylene, etc., styrenic based polymers including block copolymers of styrene and butadiene, butylene, polypropylene, polyethylene, and mixtures thereof.

Figure 2A:
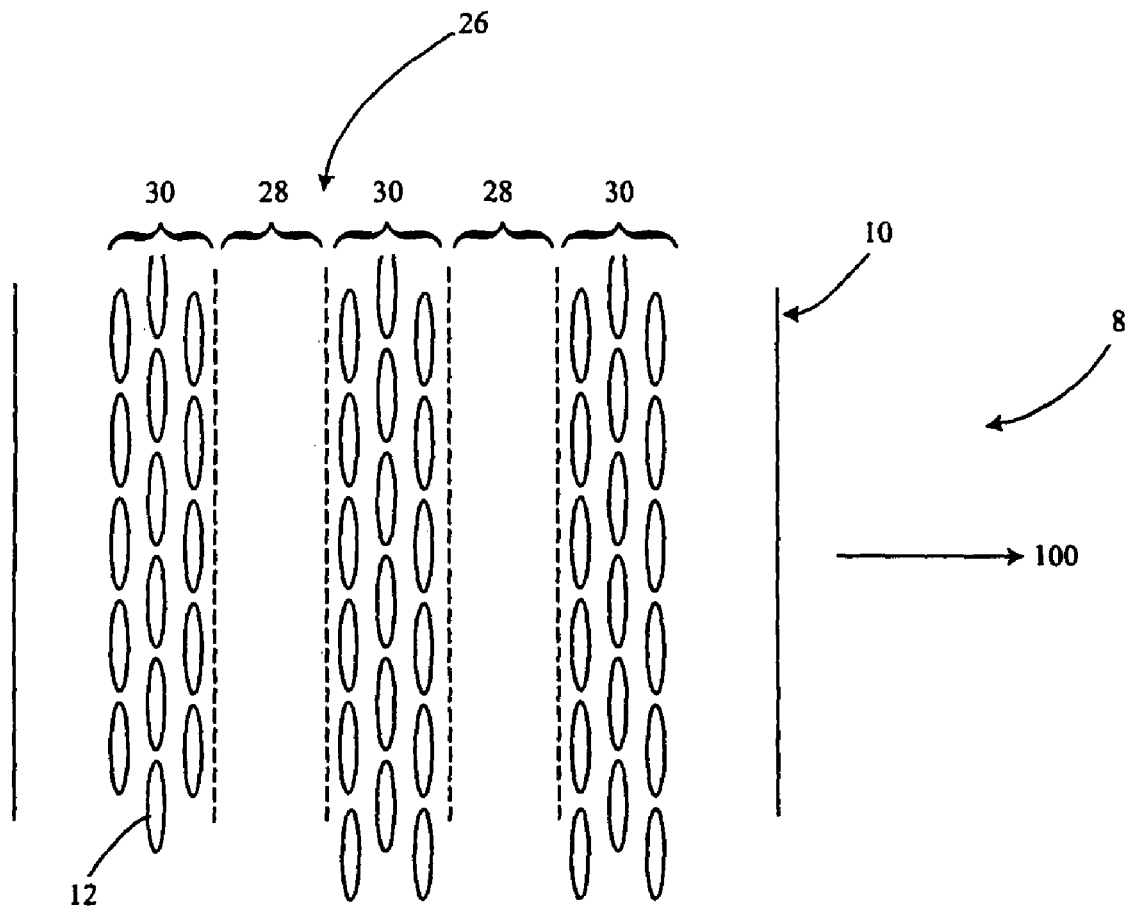
FIG. 2a is a plan view of an embodiment of this invention using lanes of unapertured film to increase the retractive force.
Figure 2B:
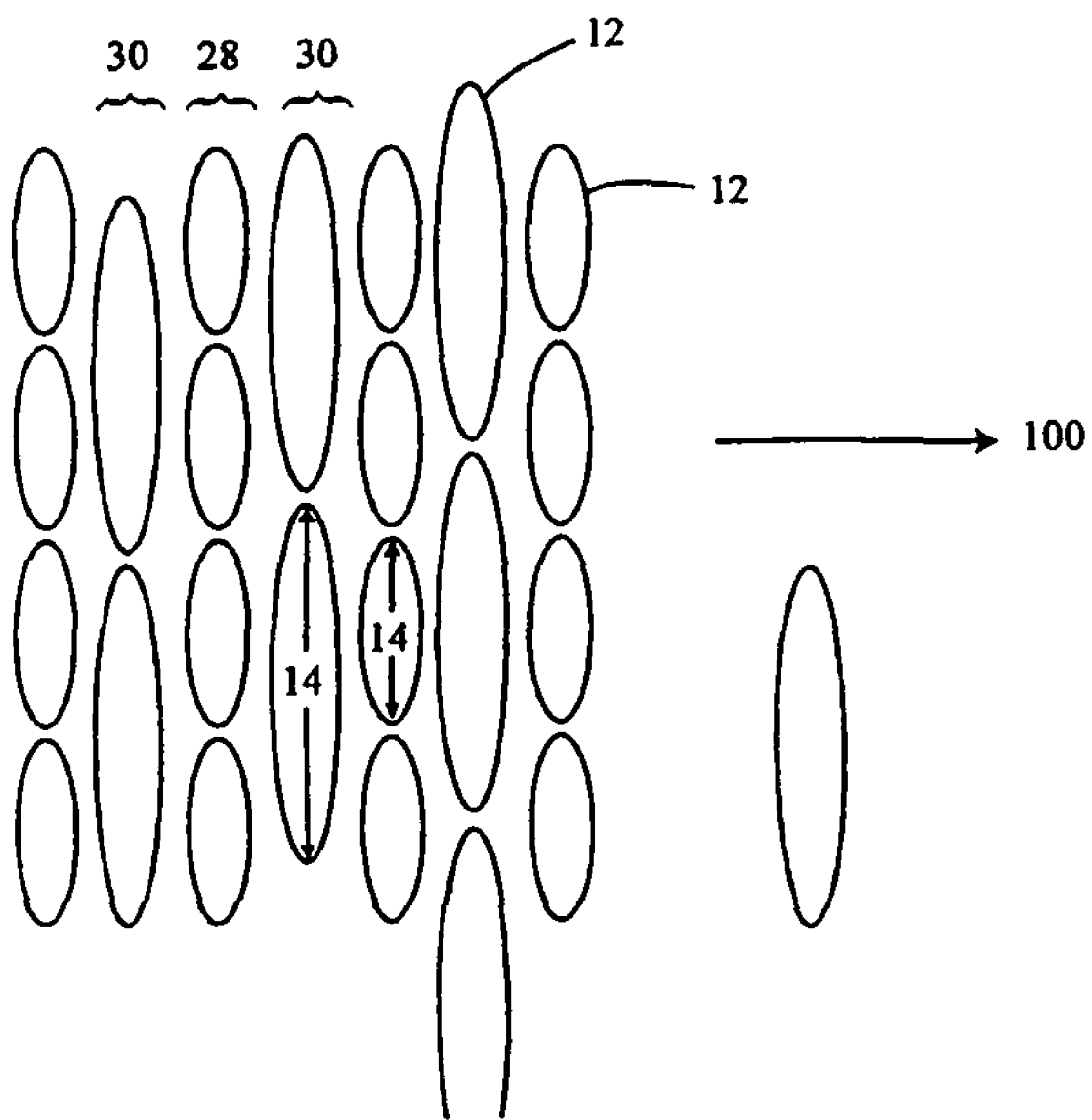
FIG. 2b is a plan view of an embodiment of this invention that uses at least two shapes of elongated cells to increase the retractive force.

As shown in FIGS. 2a and 2b, lanes 28 and 30 may be created to increase the retroactive force of web 10. In FIG. 2a, lanes 28 are two-dimensional and lanes 30 are three-dimensional. This embodiment may be prepared by vacuum- or hydro-forming a film over a screen having rows of perforations separated apart from one another by un-perforated screen material. In FIG. 2b, lanes 28 have smaller cells while lanes 30 have larger cells. The smaller cells in lane 28 need not have the same shape, size or relative axes ratios to the larger cells in lane 30, that normally will have the size, shape & relative axes ratios described herein. In both FIGS. 2a and 2b, lanes 28 increase the retractive force. In both FIGS. 2a and 2b, the direction of elongation 100 is orthogonal to the elongated cells 12.

The retractive force mechanism 26 illustrated in FIG. 2a includes lanes of two-dimensional material 28 between lanes of three-dimensional elongated cells 30. The entire web 8 is constructed of netting material 10 wherein cells 12 only exist in three-dimensional lanes 30 and are separated by two-dimensional lanes 28. The relative width of two-dimensional lanes 28 and three-dimensional lanes 30 may vary upon application, but in a preferred embodiment, the three-dimensional lanes 30 and two-dimensional lanes 28 are of the same width.

The retractive force mechanism 26 illustrated in FIG. 2b includes small cell lanes 28 between large cell lanes 30. The cells 12 in lanes 28 are smaller than cells 12 in lanes 30 and provide increased retractive force. In addition to the specifically preferred embodiments illustrated in FIGS. 2a and 2b, lanes 28 may be comprised of three-dimensional unapertured cells 12, while lanes 30 may include apertured elongated cells 12. Such unapertured cells 12 may be similar in shape to the apertured elongated cells 12 to provide a continuity in texture.

Figure 3A:
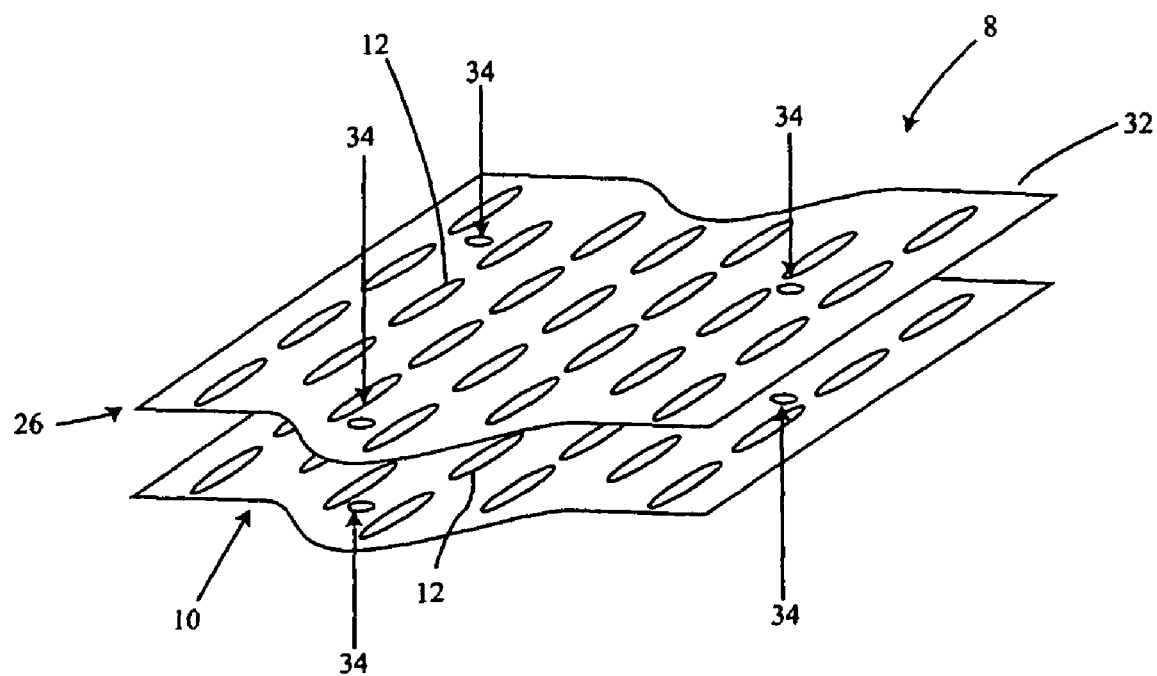
FIG. 3a is an isometric view of an embodiment of this invention wherein two films of FIG. 1 are combined to increase the retractive force.

The retractive force mechanism 26 illustrated in FIG. 3a includes a second reinforcing layer of web 10 bonded to existing formed web 10. The two formed webs are preferably point bonded and preferably aligned such that the elongated apertures are aligned parallel to one another although not necessarily an exact overlap. For some applications, it may be desirable to offset the retractive force mechanism 26 from formed film 10 so that the apertures are not exactly parallel. For example, an offset of approximately 10° may be desired. The second layer of formed web 10 is referred to in FIG. 3a as reinforcing layer 32. Reinforcing layer 32 preferably is point bonded to formed web 10 by discrete bonds 34. Discrete bonds 34 may be created by a variety of point bonding methods as required by the application or the materials being used. The direction of elongation 100 generally is orthogonal to cells 12.

Figure 3B:
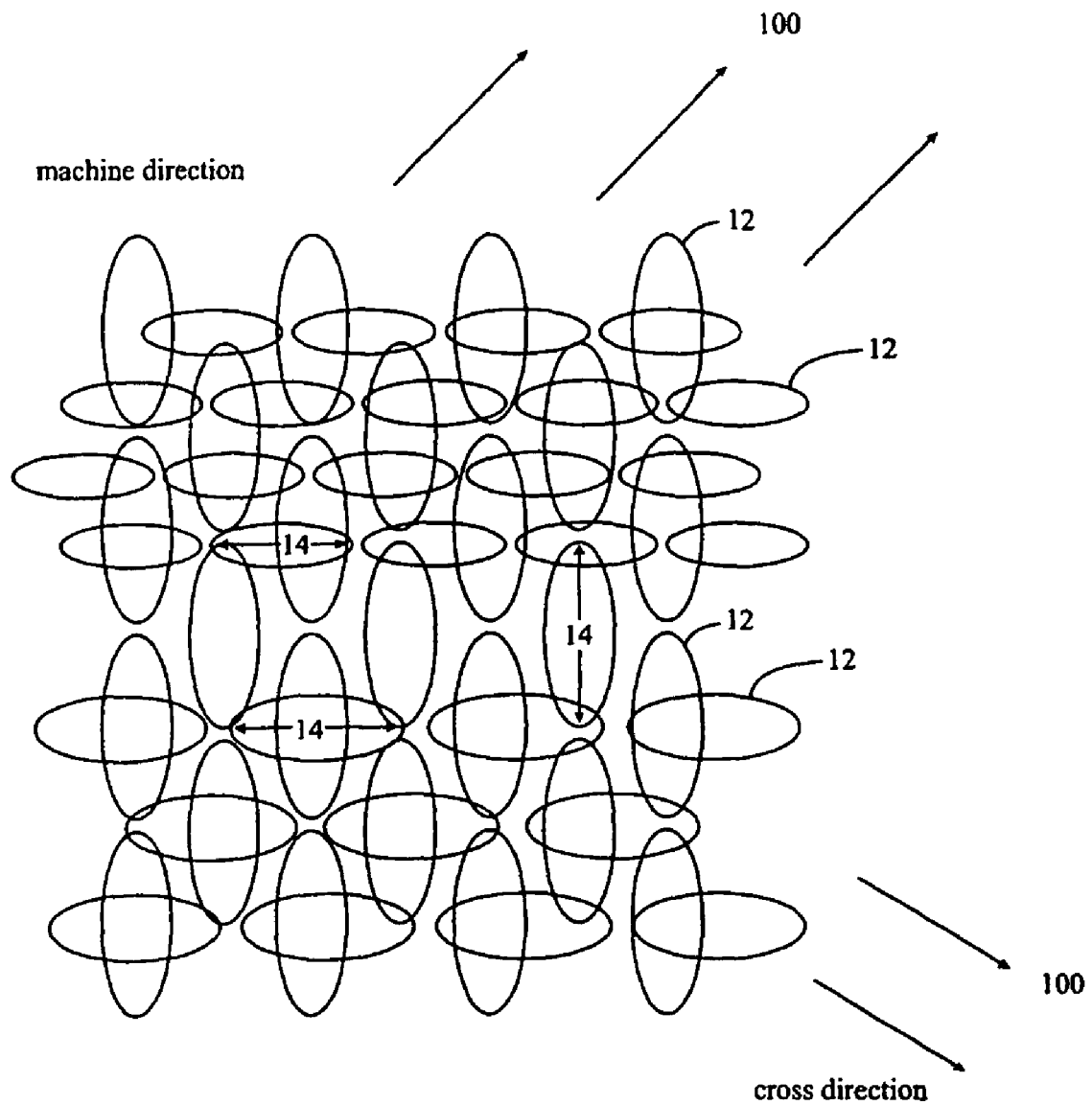
FIG. 3b is a plan view of two embodiments of this invention wherein two overlapping layers of web material are overlaid at an angle to one another, in one embodiment the layers have similar cell sizes while in the other they have different cell sizes.

Alternatively, reinforcing layer 32 may be positioned with cells 12 orthogonal to cells 12 of web 10, as shown in FIG. 3b. The cells 12 of reinforcing layer 32 may be the same size as the cells 12 of web 10, as shown in the lower portion of FIG. 3b. The cells 12 of reinforcing layer 32 may be of different size than cells 12 of web 10, as shown in the upper portion of FIG. 3b. The directions of elongation 100 are generally at 45° angles to cells 12.

Figure 4A:
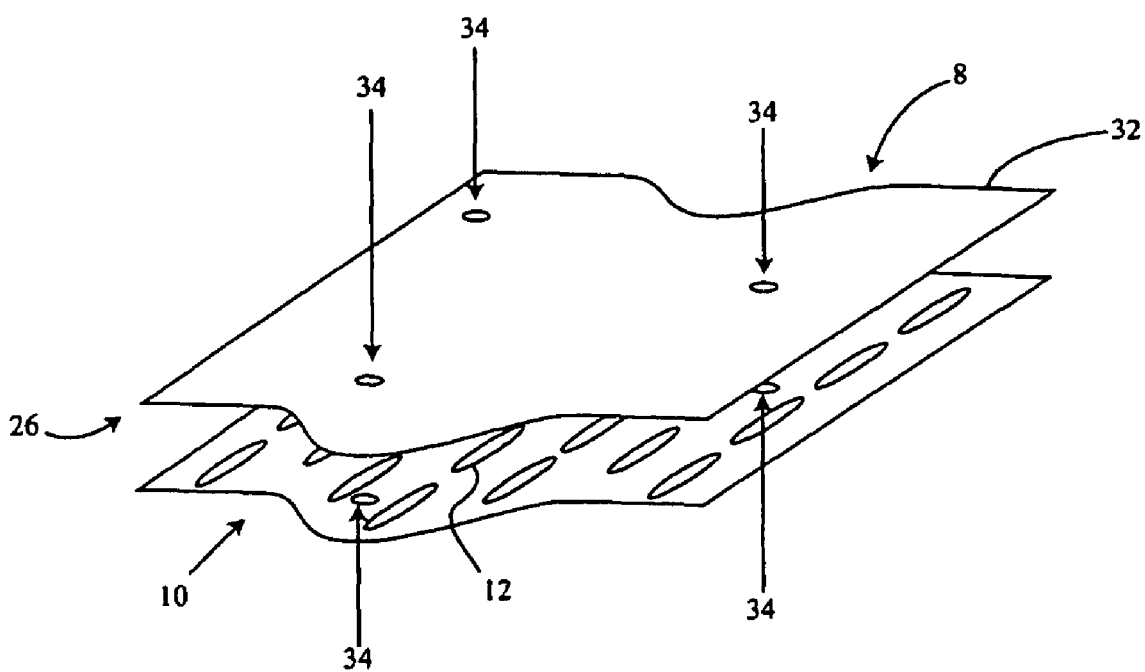
FIG. 4a is an isometric view of an embodiment of this invention wherein a reinforcing layer is attached to the web of FIG. 1 to increase the retractive force.

Referring now to FIG. 4a, the retractive force mechanism 26 preferably is a reinforcing layer 32, but reinforcing layer 32 may be comprised of a variety of materials other than the materials used to form web 10. In particular, it is believed that reinforcing layer 32 may be a film, a non-woven, a necked non-woven, an incrementally stretched non-woven, a two-dimensional apertured non-woven, a slit non-woven, a woven material, apertured film, apertured film with elongated apertures, laminates or other materials that will increase the retractive force of formed web 10 without adversely affecting the stretchability of formed web 10. In particular, necked non-wovens are effective reinforcing layer 32 materials. Reinforcing layer 32 preferably is bonded to formed film 10 by discrete point bonds 34. Discrete bond 34 can be created by a variety of point bonding methods depending upon the application and the material being used, and skilled artisans are capable of creating discrete bonds 34 by any of these methods, using the guidelines provided herein and techniques known in the art.

Figure 4B:
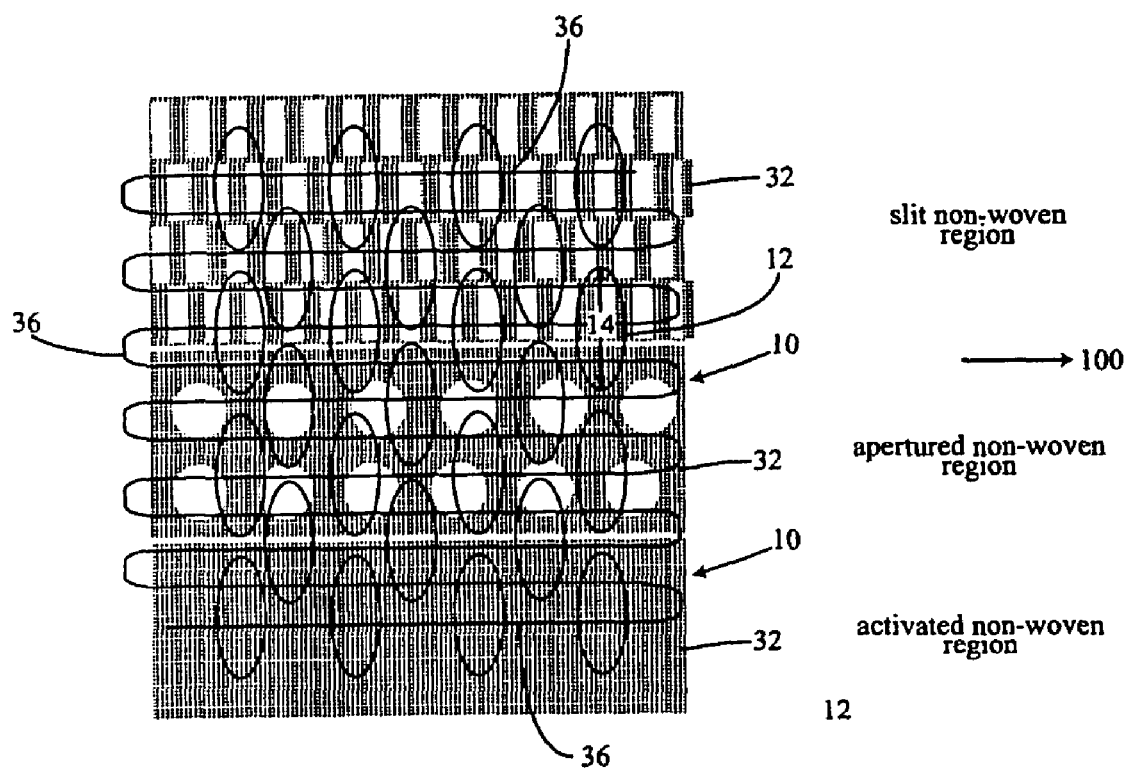
FIG. 4b is a plan view of three embodiments of this invention wherein a non-woven reinforcing layer is attached to the web of FIG. 1 to increase the retractive force, a first non-woven with slits, a second one with apertures and the third one with IMG activation.

FIG. 4b illustrates three different reinforcing layers (from top to bottom): (i) a slit non-woven; (ii) a two-dimensional apertured non-woven; and (iii) an incrementally stretched (or "activated") non-woven. This figure also illustrates the reinforcing layers 32 bonded to web 10 with an adhesive or an elastic adhesive 36 in a back and forth pattern, or zig-zag pattern.

Figure 5:
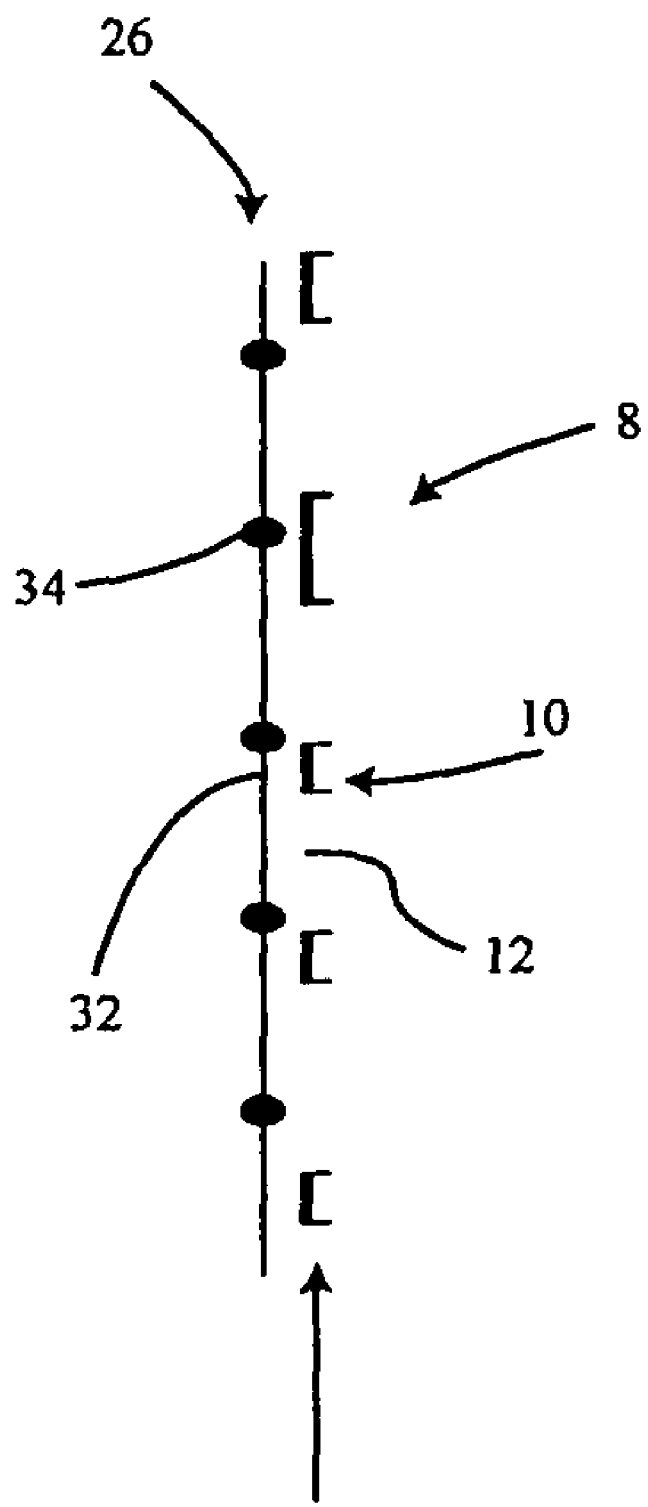
FIG. 5 is a cross-sectional view of the material shown in FIG. 4.

FIG. 5 is a cross-section of stretchable web 8 shown in FIG. 4a. The retractive force mechanism 26 comprising the reinforcing layer 32 preferably is bonded to the formed film layer 10 with a plurality of discrete point bonds 34. As shown in FIG. 5, discrete point bonds 34 may not always create a bond between formed film 10 and reinforcing layer 32 because they may fall in the apertures 12 of formed film 10. Such discrete bonds 34 that do not actually bond the materials together, may be useful for creating an aesthetic pattern on reinforcing layer 32, or may simply be useful in guaranteeing sufficient bonds by providing random bonding.

Referring now to FIGS. 6-10, the retractive force mechanism preferably includes a series of bridging elements 38 that extend across elongated cells 12 generally orthogonal to their length 14. Bridging elements 38 are believed to increase the retractive force in the direction of elongation 100 that is generally orthogonal to length 14 of cells 12. Thus, the retractive force mechanism also includes a bridging element in the stretchable web.

Figure 6:
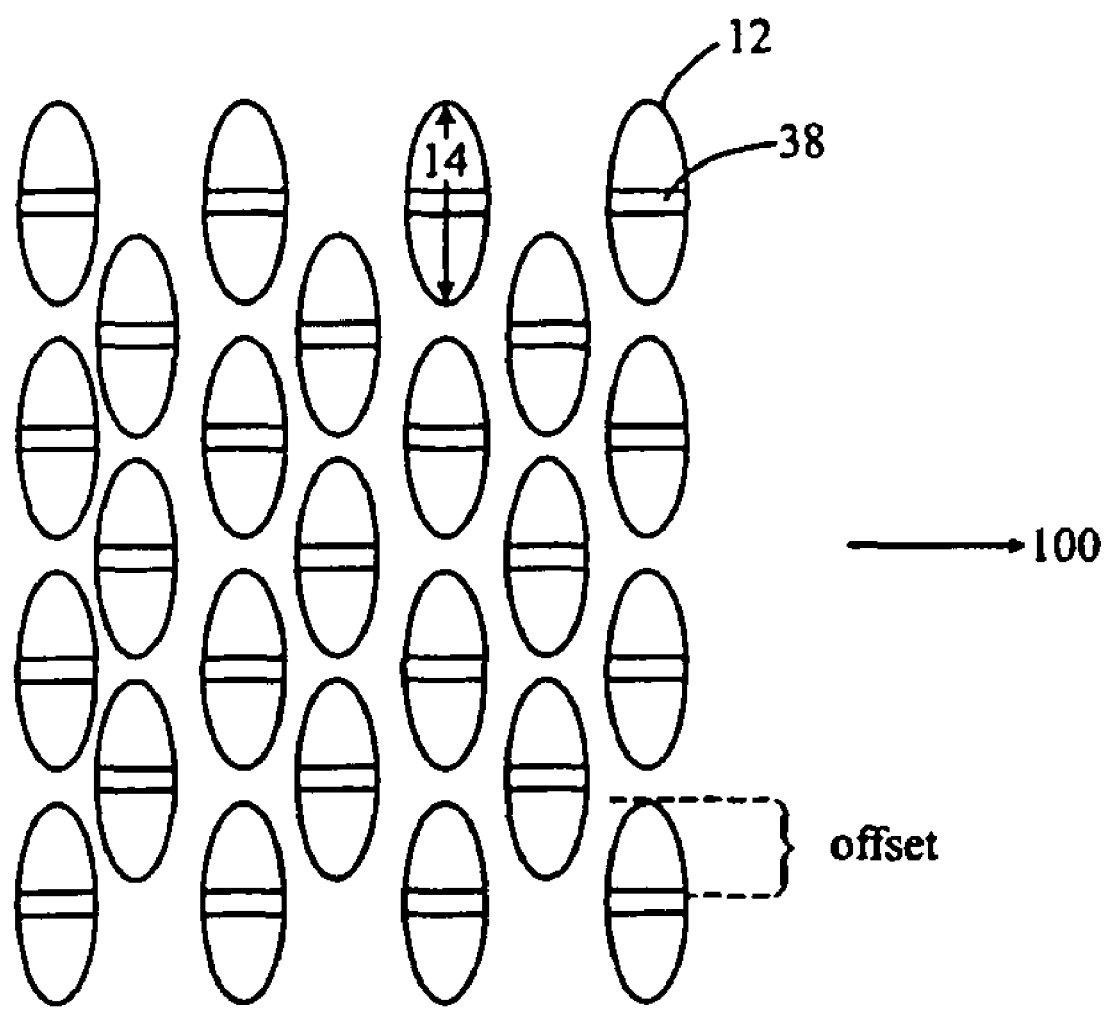
FIG. 6 is a plan view of an embodiment of this invention wherein bridging elements extend across the minor axis of the elongated cells.

Referring to FIG. 6, the cells 12 preferably exist in an evenly staggered brick pattern and the bridging elements cross the center of cells 12. In this pattern, the bridging elements 38 are offset from each other by one-half the length of cells 12. Bridging elements 38 may be two-dimensional, i.e., exist on the upper surface only, or may be three-dimensional, i.e., have walls extending in the z-direction similar to cells 12. Bridging elements 38 may be created of the same netting material as web 10, or, as is discussed in more detail below, bridging elements 38 may be formed of the same or different type of material that is subsequently deposited across or on cells 12.

Figure 7:
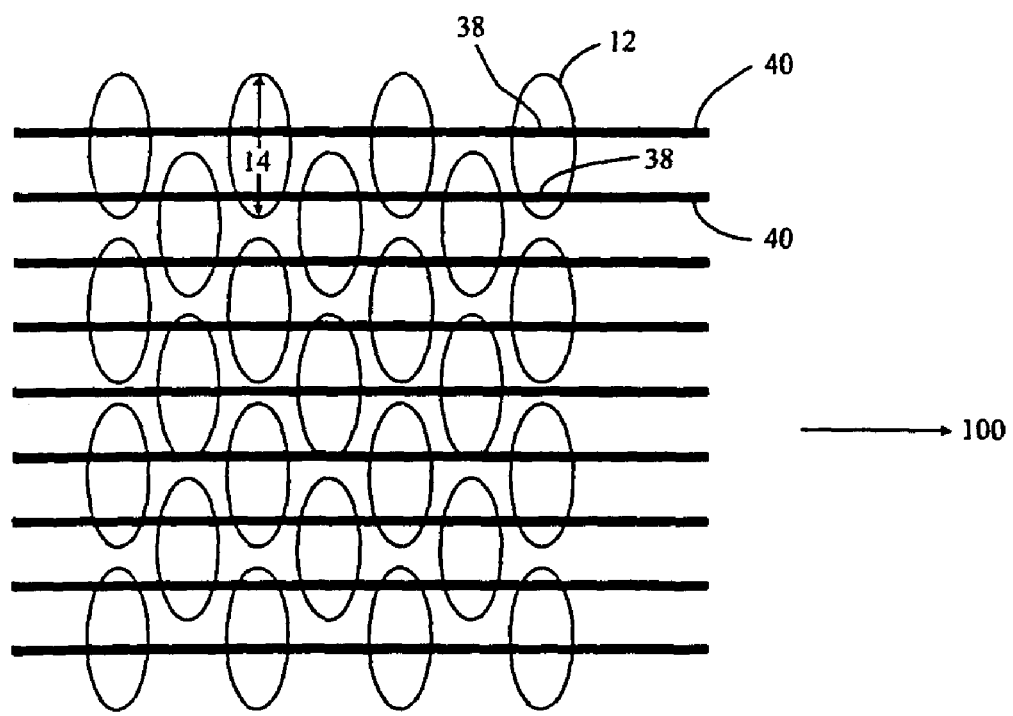
FIG. 7 is a plan view of an embodiment of this invention wherein strands of a second material are applied to the web to act as bridging elements.
Figure 8:
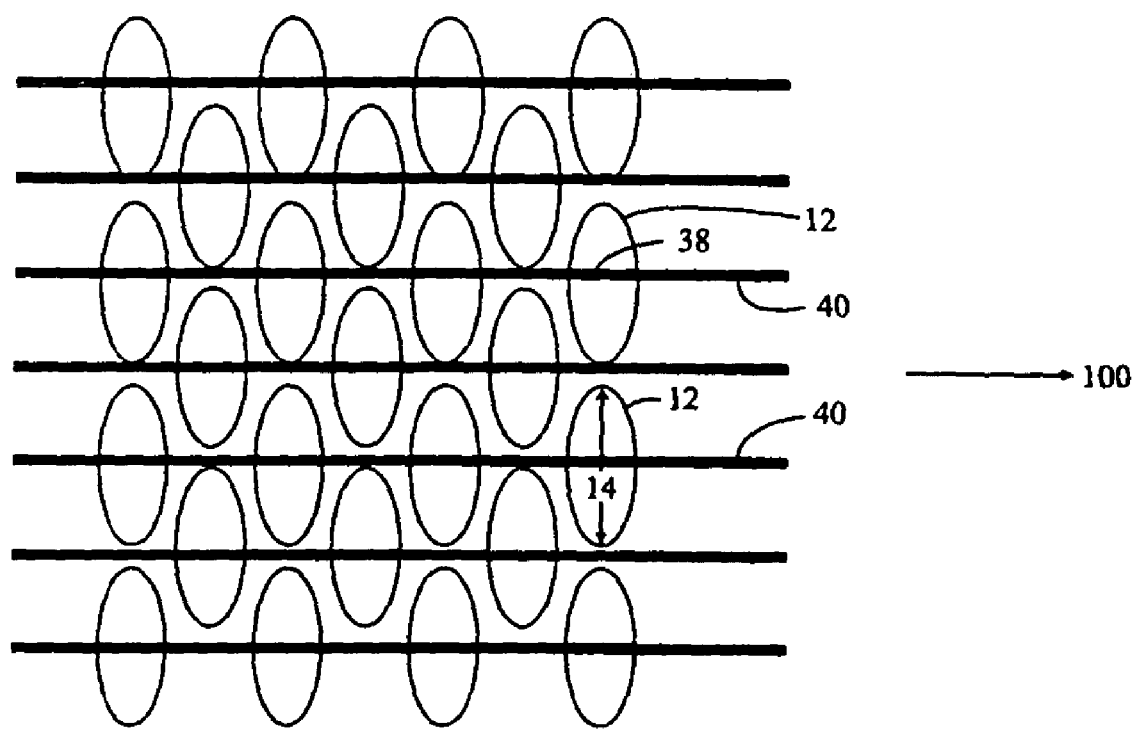
FIG. 8 is a plan view of an embodiment of this invention wherein strands of a second material are applied across the centers of the major axes of the elongated cells to act as bridging elements.

For example, FIG. 7 illustrates strands 40 of added material that are applied parallel to the direction of elongation 100 and orthogonal to the length 14 of cells 12. Strands 40 may be comprised of any material that may bond to web 10, in particular adhesives and elastomeric adhesives as discussed in more detail below, including film strips and non-woven strips. Strands 40 preferably are arranged without reference to cells 12, except that they are orthogonal to length 14, thus creating bridging elements 38 in various positions on cell 12. In FIG. 8, however, strands 40 preferably are positioned such that the bridging elements 38 are centered along length 14 of cells 12.

Figure 9:
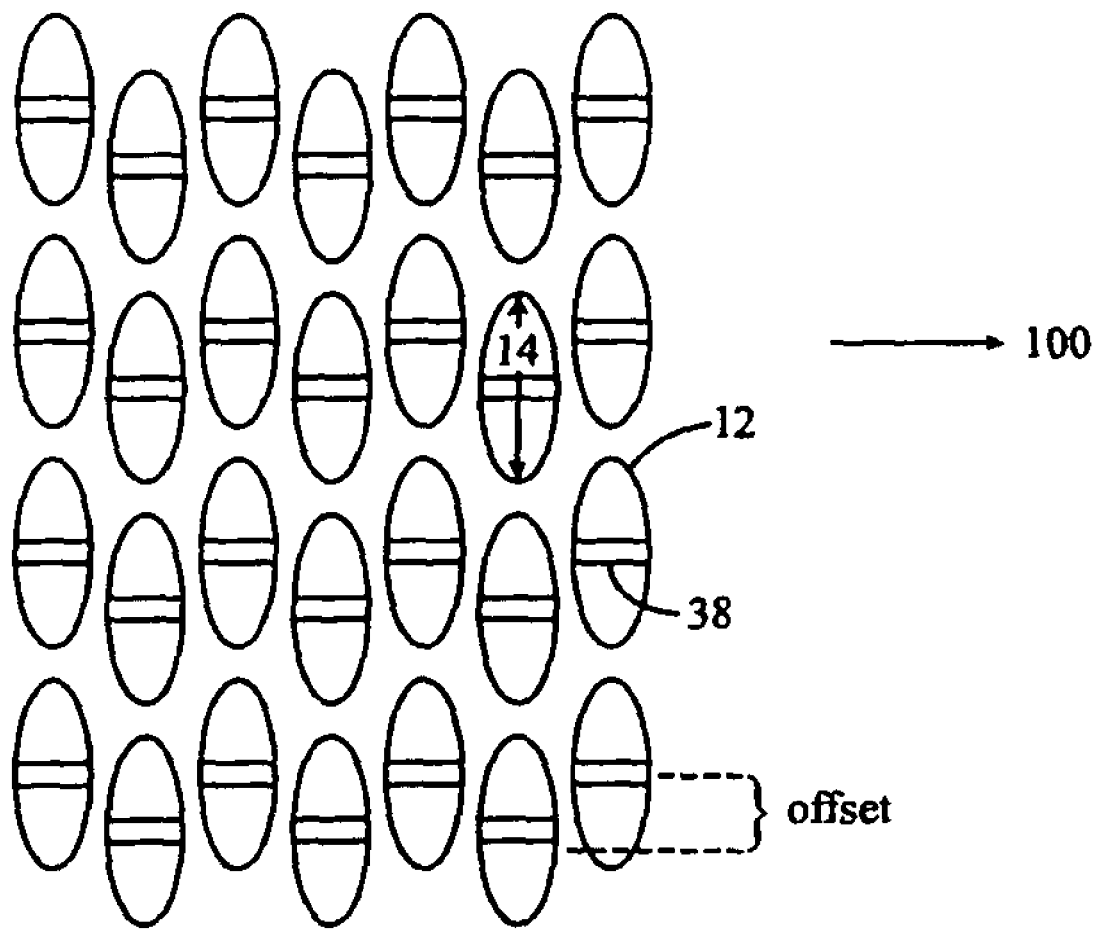
FIG. 9 is a plan view of an embodiment of this invention wherein the cells and bridging elements have a reduced offset pattern.
Figure 10:
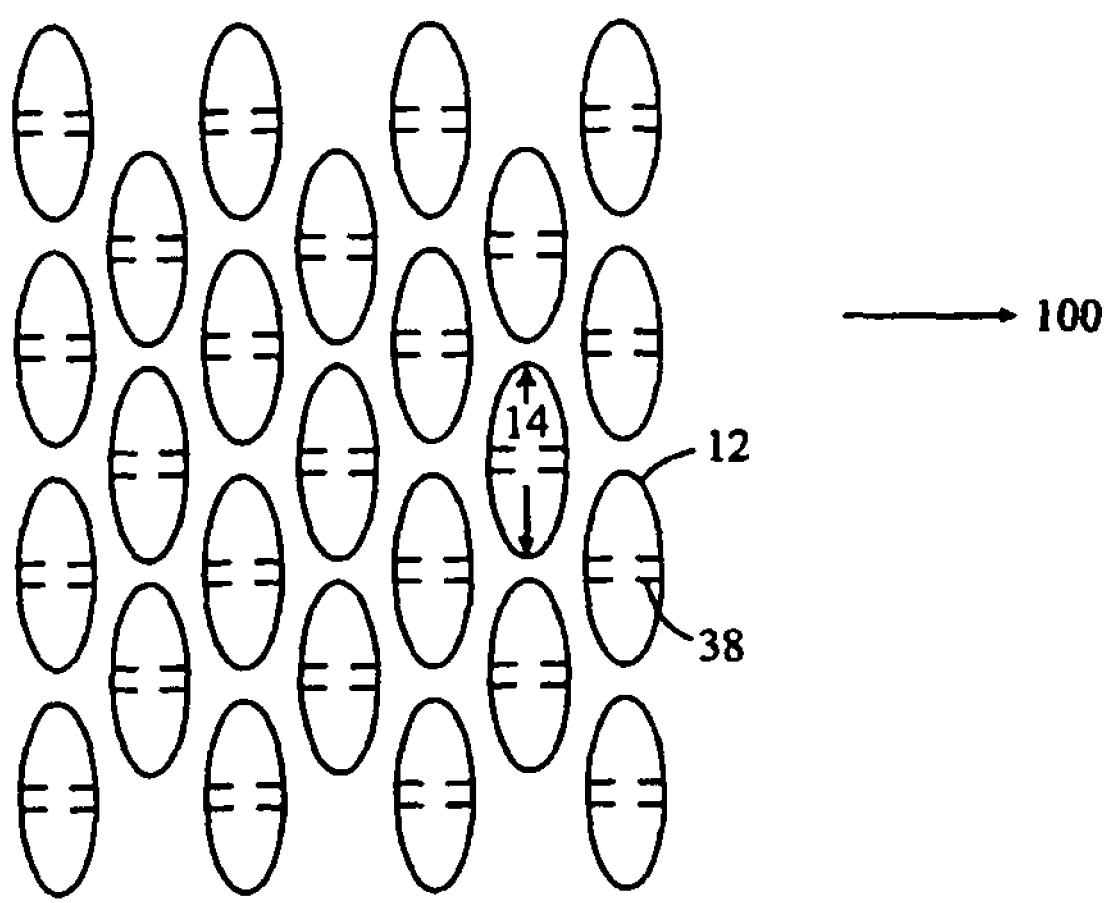
FIG. 10 is a plan view of an embodiment of this invention wherein the bridging elements are ruptured.

FIG. 9 illustrates cells 12 arranged in a less offset staggered pattern such that bridging elements 38 are offset by approximately one-quarter of length 14 of cells 12. In FIG. 10, bridging elements 38 are shown ruptured. This may be desirable where high form elasticity is desired in the product, but not during processing. For example, a web 10 with high form elasticity may include bridging elements 38 of a relatively inelastic material. Such bridging elements 38 would reduce unwanted stretching during processing of web 10. After the processing stage(s) where stretching is not desirable, the user or processor then can stretch the web 10 to a point where the bridging elements 38 rupture so that web 10 is elastic in the final product. Additionally, bridging elements 38 that rupture may allow a garment made with web 10 to fit a wider range of sizes.

Figure 11:
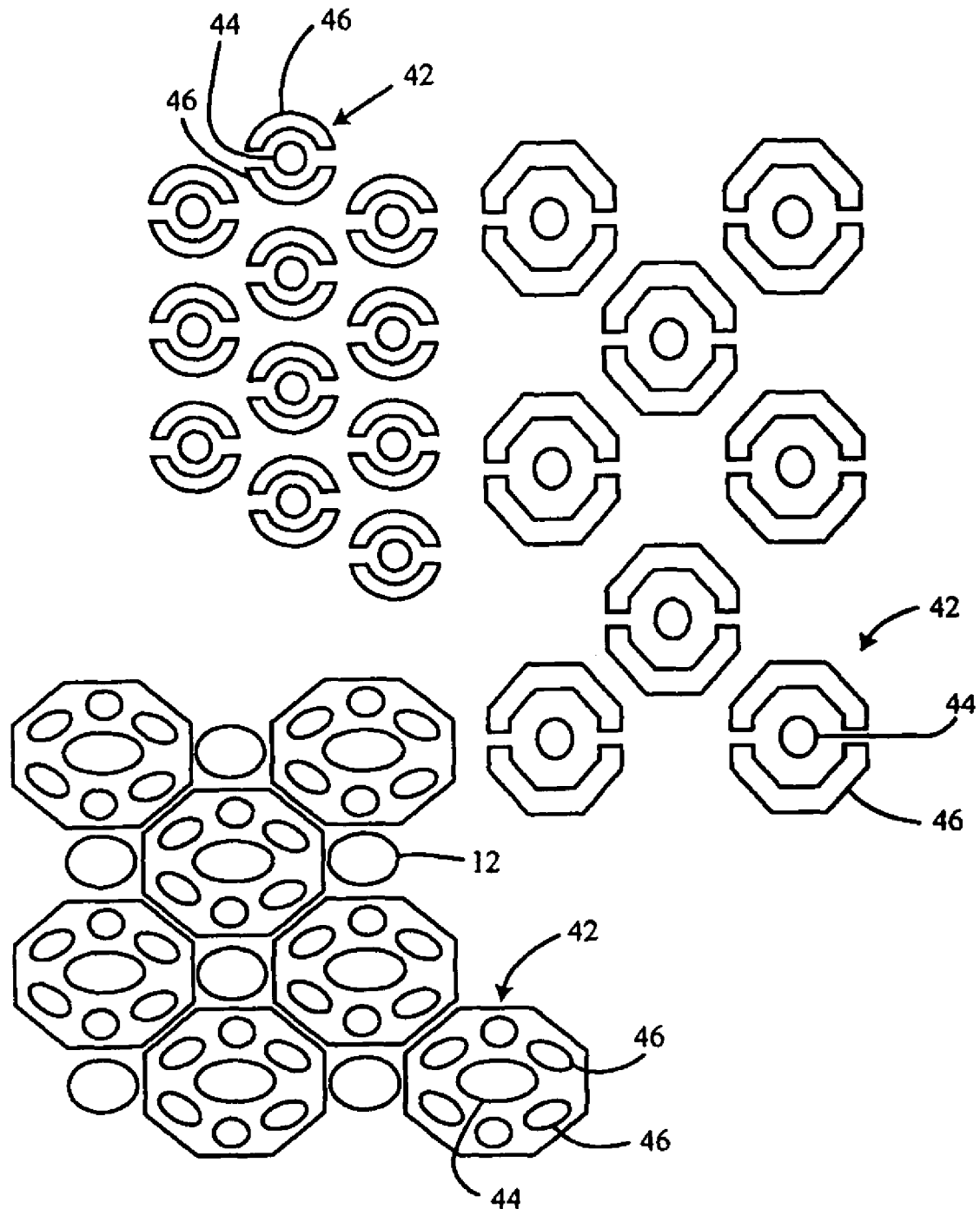
FIG. 11 is a plan view of three embodiments of this invention wherein the cells are arranged in pinwheel patterns, wherein three such patterns are shown.

FIG. 11 illustrates various groupings 42 of cells 12 that can be used to impart improved retractive force characteristics. A common feature present in these groupings 42 is a central cell 44 encircled by a plurality of partially surrounding cells 46. For example, in the groupings 42 shown in the upper left of FIG. 11, a round central cell 44 is partially surrounded by two semi-circles, or rounded "C" shaped, cells 46. The groupings in the upper right of FIG. 11 are similar, except that the partially surrounding cells 46 are more angular.

The groupings 42 illustrated in the lower left portion of FIG. 11 have an elongated central cell 44 and a plurality of surrounding apertured cells 46 (each grouping 42 is outlined for clarity). The surrounding apertured cells 46 are of various shapes. Some of the surrounding cells 46 may be curved (e.g., like a comma), while others are simply round. Between the groupings 42 are cells 12 that are not a part of any particular grouping 42. The various pinwheel designs shown act as a cell 12 within a cell 12, thereby providing improved formed elasticity performance.

The present invention now will be explained with reference to the following example, which is not intended to limit the invention.

EXAMPLE

Table 1 shows the effect on the hysteresis properties of the netting material with retractive force mechanisms in three different conditions: (i) when the oval cell is by itself—"control;" (ii) when two layers of oval cells are overlaid on top of each other; and (iii) when a reinforcing layer of oval cells are at a 30° degree angle to the web.

The following materials were used to form the samples depicted in the Table:

Control sample: 1 mil thickness, 10:1 L/D Holes, 5.5 per inch in the transverse direction. This results in a nested brick pattern as shown in FIG. 1 with 36% open area. Formula: 86.3% Chevron 4571 high density polyethylene (HDPE), 5.7% A110313 ($TiO_2$ concentrate), 3% P3155 (Surfactant Concentrate), 5% Exxon P3155 (PP);

Sample 1: Two layers of the Control sample adhesively attached with the long axis of the holes in the top layer parallel to the long axis of the holes in the bottom layer.

Sample 2: Two layers of the Control adhesively attached with the long axis of the holes in the top layer aligned 30 degrees off parallel with the long axis of the holes in the bottom layer.

Each sample above was stretched on a tensile tester MTS, model number 27.00095 with TestWork software, commercially available from MTS Sytsems, Minneapolis, Minn. The MTS unit included a 100N load cell, and the materials were tested using a 2-cycle 100% elongation hysteresis. The gauge length was 50 mm, cross-head speed was 20 in/min., and there was no holding time between the load and unload cycles. The values are reported in Table 1 below. A higher value (gm-force/in) reported in the table denotes a higher retractive force.

TABLE 1

|  | Control | Sample 1 | Sample 2 |
| --- | --- | --- | --- |
| First Cycle Load |  |  |  |
| 20% Elongation | 9.95 | 82.40 | 51.80 |
| 40% Elongation | 10.80 | 129.92 | 56.95 |
| 60% Elongation | 13.26 | 179.13 | 73.13 |
| 80% Elongation | 26.66 | 242.24 | 131.37 |
| $1^{st}$ peak Load | 27.33 | 220.83 | 131.98 |
| First Cycle Unload |  |  |  |
| 20% Elongation | −0.39 | −0.96 | −0.88 |

TABLE 1-continued

|  | Control | Sample 1 | Sample 2 |
| --- | --- | --- | --- |
| 40% Elongation | −0.85 | −1.03 | −0.82 |
| 60% Elongation | −0.09 | −0.93 | −0.84 |
| 80% Elongation | 6.92 | 89.94 | 31.52 |
| $2^{nd}$ Cycle Load |  |  |  |
| 20% Elongation | 7.52 | −0.28 | 0.59 |
| 40% Elongation | 6.81 | 13.16 | 8.93 |
| 60% Elongation | 8.62 | 44.46 | 20.77 |
| 80% Elongation | 23.30 | 154.87 | 110.60 |
| $2^{nd}$ Peak Load | 24.84 | 155.68 | 118.52 |
| $2^{nd}$ Cycle Unload |  |  |  |
| 20% Elongation | −0.74 | −0.79 | −0.75 |
| 40% Elongation | −0.53 | −0.66 | −0.94 |
| 60% Elongation | −0.09 | −0.78 | −0.88 |
| 80% Elongation | 6.60 | 35.17 | 28.25 |
| Unload Peak Load | 14.55 | 62.00 | 61.26 |
| $2^{nd}$ Cycle Permanent Set | 5.84 | 33.98 | 30.63 |

The data in table 1 shows that incorporating a reinforcing layer provides excellent retractive force for the netting material when it is stretched in a given direction. The combination of double identical layers of oval cells overlaid on top of each other (Sample 1) resulted in load and unload forces that were at least 5 times greater than the control sample. Since the sample has two identical layers, one might expect to see a two-fold increase in force, but Sample 1 provided a 5-fold increase, which is unexpected. This result suggests enhanced retractive force arises with two layers overlaid on top of each other. When reinforcing layers of oval cells were at a 30 degree angle, (Sample 2) the load and unload forces were at least 3 times greater than the control sample. In the second cycle, the load and the unload forces were much less than that in the first cycle and the applied force varied proportionately at different percentage of elongation as in the first cycle. Thus, these results indicate that the netting material with two layers of oval cells has the requisite retractive force to provide improved stretchability and good recovery characteristics.

While particular embodiments of the present invention have been illustrated and described, it should be recognized that the examples of the preferred embodiments have been limited to certain configurations of the stretchable web. Those skilled in the art would recognize that various changes and modifications can be made to the preferred embodiments described herein without departing from the spirit and scope of the invention.

We claim:

1. A stretchable web comprising:
    a web having a first plurality of three-dimensional elongated cells, wherein said cells have a major and minor axes and an aspect ratio of about 5 to about 15, and are aligned in spaced-apart lanes along their major axes to provide mechanical elasticity in a direction perpendicular to their alignment, and
    a retractive force mechanism disposed so as to provide increased retractive force to the first plurality of elongated cells in a direction opposite of said mechanical elasticity, wherein said retractive force mechanism comprises a second three-dimensional web bonded to the first web, wherein said second web has a second plurality of elongated cells that have an aspect ratio of about 5 to about 15 and that are aligned in spaced-apart lanes along their major axes, said alignment being nonparallel to the alignment of the first plurality of elongated cells.

2. The stretchable web of claim 1 wherein said alignment of the second plurality of cells is offset from said alignment of the first plurality of cells by about 100 degrees.

3. The stretchable web of claim 1 wherein said alignment of the second plurality of cells is orthogonal to said alignment of the first plurality of cells.

4. The stretchable web of claim 1 wherein said alignment of the second plurality of cells is in the machine direction and said alignment of the first plurality of cells is in the cross direction.

5. The stretchable web of claim 1 wherein said second plurality of cells are spatially smaller than said first plurality of cells.

6. The stretchable web of claim 1 wherein said second plurality of cells have an aspect ratio that is smaller than the aspect ratio of said first plurality of cells.

* * * * *